United States Patent [19]

Nyquist et al.

[11] 4,281,421
[45] Aug. 4, 1981

[54] PASSIVE DOSING DISPENSER WITH IMPROVED HYPOCHLORITE CAKE

[75] Inventors: John D. Nyquist; David J. Kitko; Richard F. Stradling, Jr., all of Cincinnati, Ohio

[73] Assignee: The Procter & Gamble Company, Cincinnati, Ohio

[21] Appl. No.: 19,547

[22] Filed: Mar. 12, 1979

[51] Int. Cl.³ .............................................. E03D 9/02
[52] U.S. Cl. .......................................... 4/228; 4/227; 252/95; 252/99; 252/187 H; 422/261; 422/264; 422/266; 422/277; 423/474; 424/149
[58] Field of Search ....................... 252/187 H, 95, 99; 4/228, 227; 422/277, 261, 264, 266, 37; 423/474; 424/149

[56] References Cited

U.S. PATENT DOCUMENTS

| | | | |
|---|---|---|---|
| 2,023,459 | 12/1935 | Bachman | 210/28 |
| 2,534,781 | 12/1950 | MacMahon | 252/99 |
| 2,695,274 | 11/1954 | MacMahon | 252/99 |
| 3,036,013 | 5/1962 | Jaszka et al. | 252/99 |
| 3,061,842 | 11/1962 | Woodruff | 4/225 |
| 3,121,236 | 2/1964 | Yadro et al. | 4/228 |
| 3,154,495 | 10/1964 | Robson et al. | 252/99 |
| 3,234,141 | 2/1966 | Robson | 252/187 H |
| 3,276,949 | 10/1966 | Robson et al. | 252/187 H |
| 3,297,578 | 1/1967 | Crutchfield | 252/187 R |
| 3,441,507 | 4/1969 | Schiefor | 252/187 R |
| 3,491,028 | 1/1970 | Crotty et al. | 252/103 |
| 3,503,884 | 3/1970 | Chirash et al. | 252/95 |
| 3,518,201 | 6/1970 | Wessels | 252/99 |
| 3,560,396 | 2/1971 | Robson | 252/187 H |
| 3,562,165 | 2/1971 | Altieri | 252/102 |
| 3,604,020 | 9/1974 | Molso | 4/228 |
| 3,755,179 | 8/1973 | Fitzgerald | 252/187 H |
| 3,758,409 | 9/1973 | Nakagawa et al. | 252/187 H |
| 3,793,216 | 2/1974 | Dychdala | 252/187 H |
| 3,998,751 | 12/1976 | Murray | 252/187 H |
| 4,064,572 | 12/1977 | Wicks | 4/227 |
| 4,171,546 | 10/1979 | Dirksing | 4/227 |

FOREIGN PATENT DOCUMENTS

| | | |
|---|---|---|
| 76 | 6/1978 | European Pat. Off. |
| 5286 | 4/1979 | European Pat. Off. |
| 1126108 | 9/1968 | United Kingdom |
| 1175749 | 12/1969 | United Kingdom |
| 1538857 | 1/1979 | United Kingdom |

Primary Examiner—Edward A. Miller
Assistant Examiner—Irwin Gluck
Attorney, Agent, or Firm—Leonard Williamson; Ronald L. Hemingway; Richard C. Witte

[57] ABSTRACT

The combination of a passive dosing dispenser, of the type having a reservoir containing a cake of active ingredients which are depleted as water is routed through the dispenser, and an improved hypochlorite cake for use therein. The improved hypochlorite cake provides water-soluble hypochlorites, and additionally contains materials capable of forming a water-insoluble matrix from which hypochlorite salts may be leached out by the water in the reservoir. The size of the cake desirably increases somewhat while the dispenser is in use so that the mass of aqueous hypochlorite which may be poured from the reservoir of the dispenser remains constant or slightly decreases as the active ingredients are used up. This improvement levels the delivery of hypochlorite over a long period of time, and additionally minimizes the amount of chlorine gas which may be released if the hypochlorite containing solution within the dispenser of the present invention is inadvertently brought into contact with organic matter such as waste paper.

11 Claims, 8 Drawing Figures

PASSIVE DOSING DISPENSER WITH IMPROVED HYPOCHLORITE CAKE

TECHNICAL FIELD

The most specific technology to which this invention relates is that of disinfecting devices adapted to dispense hypochlorite disinfectant solutions to the tank of a conventional toilet when it is flushed. The invention relates more generally to dispensers of the type which receive a liquid in an internal reservoir and contact the liquid with a cake of active ingredients in the reservoir to form a solution which is subsequently dispensed. The invention provides means to reduce or level the pourable fluid capacity of the dispenser, while maintaining its hypochlorite delivery, as the cake of active ingredients is expended.

BACKGROUND ART

Dispensers which are adapted to deliver disinfecting or aesthetic ingredients to a toilet tank to condition water in the toilet tank and bowl are well known in the prior art, as are dispensers which are described hereinafter as "passive" in that they require no moving parts but deliver a disinfecting or aesthetic solution responsive to the flushing of a toilet at the usual intervals.

A patent application owned by the owners of the present application, Ser. No. 897,477, filed by Dirksing, on Apr. 18, 1978, (especially FIGS. 12-19 and the accompanying text) discloses an especially desirable toilet tank dispenser which receives water from a toilet tank in which it is immersed as the tank water rises after a previous flush, transmits this water to an internal receiver which is isolated by an air lock from the tank water when the toilet is full, contacts the water in the reservoir with a cake containing active ingredients such as hypochlorite to form a hydrochlorite solution, stores this hypochlorite solution in the reservoir, and releases this hypochlorite solution to the toilet tank water responsive to the lowering of the level of water in the toilet tank when the toilet is flushed. This hypochlorite dispensing system is well adapted to a consumer product which may be used to condition toilet tank and bowl water. The absence of any moving parts in the dispenser makes it possible to produce a dispenser very inexpensively, as by thermoforming two halves and sealing them together. Such a dispenser may be made so cheaply that it is well adapted for use as a disposable dispenser which may be discarded after the active ingredients sealed therein are depleted.

Two problems have been noted with prior art hypochlorite cakes which are adapted to be placed inside the reservoir of a toilet tank dispenser for the purpose described above. The first of these problems is that a compressed solid cake of material containing soluble hypochlorites tend to deliver a high level of available chlorine initially, so that much of the available chlorine is released in a relatively short time. The remaining available chlorine in then released much more slowly. Thus, prior art dispensers do not deliver a relatively consistent amount of available chlorine over a long period of time. The following references contain discussions of this problem in other arts: U.S. Pat. No. 3,154,495, issued to Robson et al. on Oct. 27, 1964; U.S. Pat. No. 3,036,013, issued to Jaszka et al., on May 22, 1962; U.S. Pat. No. 3,234,141, issued to Robson on Feb. 8, 1966; U.S. Pat. No. 2,023,459, issued to Bachman on Dec. 10, 1935. (It will be noted that none of the above references deals with hypochlorite containing compositions for use in a toilet tank.)

A second problem which has been noted for hypochlorite cakes used in connection with prior art passive dosing dispensers is the tendency for the pourable fluid capacity (as defined hereinafter) of the dispenser reservoir to increase as active ingredients in the solid cake are successively dissolved and removed from the dispenser during the life cycle of the product. As a result of this increase in pourable fluid capacity, a dispenser which has been in use for some time contains a relatively large mass of hypochlorite solution, compared to the quantity contained in the reservoir during the early part of the usage life of the dispenser. When the dispenser is subsequently placed in contact with organic material, such as by storing it in a wastepaper basket for future disposal, this mass of hypochlorite solution may escape from the dispenser, come into contact with the organic matter in the wastepaper basket and oxidize this organic matter while releasing chlorine gas to the atmosphere surrounding the wastepaper basket. This problem usually occurs when a dispenser is discarded prematurely, before its active ingredients have been depleted.

The instability of hypochlorite containing compositions, particularly those containing calcium hypochlorite, is generally known. See, for example, U.S. Pat. No. 3,793,216, issued to Dychdala on Feb. 19, 1974, and U.S. Pat. No. 3,560,396, issued to Robson on Feb. 2, 1971. The chlorine releasing reaction is believed to take place in three steps as follows:

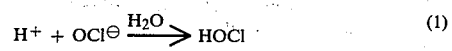

$$H^+ + OCl^\ominus \xrightarrow{H_2O} HOCl \tag{1}$$

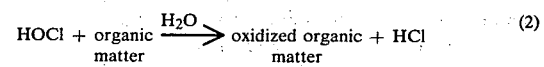

$$HOCl + \text{organic matter} \xrightarrow{H_2O} \text{oxidized organic matter} + HCl \tag{2}$$

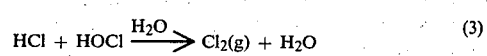

$$HCl + HOCl \xrightarrow{H_2O} Cl_2(g) + H_2O \tag{3}$$

It has been found that, when hypochlorite solutions from the preferred toilet tank dispensers are brought into contact with organic matter such as paper toweling, an appreciable quantity of chlorine gas is released and the reacting mass may heat up to nearly the boiling temperature of water. (An example of the reaction of hypochlorite solutions with paper toweling is given in one of the examples below.) The problem of reducing the release of chlorine and evolution of heat when a toilet tank dispenser is thrown away and brought into contact with organic matter is not dealt with in the prior art. Accordingly, it is an object of the present invention to reduce this problem by providing a hypochlorite cake composition which is adapted to act in conjunction with the dispenser to limit the quantity of available chlorine which the dispenser can release when it is discarded, and as a result placed in contact with organic matter.

Other objects of the present invention, although not limited by their enumeration, are to provide an alkaline composition in solution and to level the delivery of available chlorine over a long period of time, throughout a life cycle of many flushes.

DISCLOSURE OF THE INVENTION

The invention is a dosing dispenser comprising a reservoir, a hypochlorite cake within the reservoir and means to allow water to enter the reservoir, dissolve a portion of hypochlorite to form a hypochlorite solution and contain the hypochlorite solution for release at a later time, wherein the improvement resides in the provision of a hypochlorite cake containing at least one component capable of forming an insoluble porous matrix which occupies a substantial portion of the reservoir and entrains water while allowing hypochlorite ions to gradually be leached from within its boundaries and dissolved in the solution. In a preferred mode of the invention the hypochlorite cake actually expands while it is in service so that the pourable fluid capacity of the dispenser decreases as the hypochlorite is gradually exhausted from the composition.

The hypochlorite cake may be a tableted solid composition comprising the following components, expressed as percentages by weight: 5% to 84% of a hypochlorite anion; 4% to 30% of a water-soluble salt of a second anion selected from metasilicate, carbonate, and orthosilicate; and 0% to 90% of a diluent material. All of the cations present in the composition, including any cations in the diluent material which provide a substantial proportion of the composition, should form water-soluble hypochlorites, and at least one of the cations present in the composition should form a water-insoluble matrix with the said second anion.

The hypochlorite is preferably provided in the form of a salt selected from lithium hypochlorite, calcium hypochlorite, and mixtures thereof, especially a mixture wherein the ratio of lithium hypochlorite to calcium hypochlorite is between about 0.47 to 1 and about 0.17 to 1. The water-soluble salt of a second anion is selected from the water-soluble salts of metasilicate, carbonate, or orthosilicate, as well as mixtures of any of the above salts. The diluent material is not necessarily a salt, but is preferably selected from alkali metal and alkaline earth metal salts. The diluent material may optionally comprise an excess of any of the essential materials of the composition. This excess does not participate in the creation of an insoluble matrix or exchange cations with the hypochlorite anion to form a soluble hypochlorite salt.

A particular formulation which is useful to produce hypochlorite cakes for use in the present invention is as follows: about 22% calcium hypochlorite; about 8% lithium hypochlorite; about 14% sodium metasilicate; and diluent materials as the balance of the composition. In this particular embodiment of the invention the hypochlorite anion is provided by the calcium and lithium hypochlorites, the cation which is to form an insoluble matrix is a mixture of calcium and lithium cations, the second anion is metasilicate, the water-soluble salt of the second anion is sodium metasilicate, and the diluent materials are sodium chloride and the impurities in commercial grades of the hypochlorite salts. When used in combination with the dispensers described herein, the hypochlorite cakes of the present invention have been found to deliver a fairly moderate and consistent level of available chlorine to the toilet tank while slightly diminishing the pourable fluid capacity of the dispenser as active ingredients in the cakes are used up. The slight diminishment of pourable fluid capacity is due to a slight expansion of the hypochlorite cake resulting from the formation of an insoluble matrix therein. (It is also within the contemplation of the present invention to provide compositions which do not actually expand, but which merely act to prevent an increase in the pourable fluid capacity of the dispenser.) Since the pourable fluid capacity of dispensers made according to the present invention does not increase substantially as the dispersers are used, and since the available chlorine concentration in solution remains relatively steady, the present invention limits the quantity of available chlorine which can escape from the dispenser to react with wastepaper and release chlorine and heat.

DETAILED DESCRIPTION OF THE INVENTION

The following detailed description of the present invention is provided in order to enable those skilled in the art to practice the present invention. It will be understood that the scope of the invention is not limited by this disclosure, for the scope of the invention is defined by the claims appended to this specification.

In describing the present invention, the following terms will be used:

"Pourable fluid capacity" shall mean the mass of fluid which may escape from the dispenser when it is gently manipulated, such as when the dispenser is inverted or laid on its side. Portions of the solution which cannot escape to the exterior of the dispenser are not included, even if it would be possible to remove such portions of the solution by means such as forcibly disintegrating the porous matrix which remains when the available chlorine has been leached out of the hypochlorite cake.

The term "water-soluble," as used herein in relation to a composition or compound, shall mean that a saturated solution of that composition or compound provides at least the minimum concentration of the composition or compound which is effective for its intended purpose. For example, if a disinfecting solution is intended with an available chlorine content of 1.0% in aqueous solution, a hypochlorite compound intended to provide that concentration of available chlorine is considered water-soluble if a saturated solution of that hypochlorite compound provides at least 1.0% available chlorine in aqueous solution.

The term "insoluble," as used herein in relation to a composition or compound, shall mean such a composition or compound which substantially retains its solid form when it is brought in contact with a fairly large volume of water during the life of the toilet tank dispenser. Thus, in the context of a toilet tank dispenser with a hypochlorite cake, insoluble materials of the cake are those which remain as an integral part of the hypochlorite cake when the soluble ions are leached out, and which are thus never removed from the dispenser as the active ingredients are dissolved and used up.

The terms "anion" and "cation" are used to refer either to individual ions or as a collective noun to refer to an ionic species present as part of a composition. Thus, hypochlorite anion may refer either to a single moiety consisting of an oxygen atom attached to a chlorine atom and bearing a single negative charge, or to a collection of a great quantity of such ions as a distinct species in a hypochlorite cake.

First, consider the operation of the toilet tank dispenser which is the preferred environment in which to use the hypochlorite cake of the present invention in order to provide a hypochlorite solution to disinfect a toilet tank and bowl.

Figure 1:
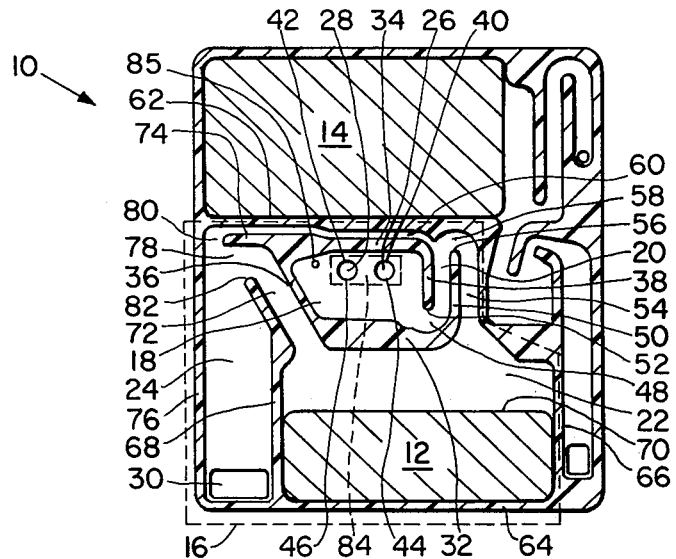
FIG. 1 is a plan view of a preferred integrated toilet tank dispenser for use with the hypochlorite cakes of the present invention.

Referring now to the figures, in which identical features are numbered identically, FIG. 1 shows a particularly desirable toilet tank dispenser which concurrently dispenses a hypochlorite solution and other ingredients (which are not relevant to the present invention) into the water of a toilet tank in which it is customarily suspended in use. In FIG. 1 an integrated dispenser 10 is shown which contains a hypochlorite cake 12 and a surfactant cake 14. The portion of integrated dispenser 10 which is enclosed by dotted line 16 is a hypochlorite dispenser which allows the mixing of the water of a toilet tank in which the dispenser is immersed with ingredients supplied by hypochlorite cake 12 to form a hypochlorite solution, and which dispenses the hypochlorite solution to the water of the toilet tank responsive to the flushing and refilling of the toilet tank. For clarity, the water which is present in integrated toilet tank dispenser 10 when it is in use is not shown in FIG. 1.

The portion of integrated dispenser 10 which is outside dotted line 16 is an independent dispenser containing a surfactant cake, which is intended to dispense a surfactant solution to the toilet tank responsive to the flushing and refilling thereof. This portion of the dispenser is shown only in order to illustrate a highly preferred embodiment of a toilet tank dispenser which is used in conjunction with hypochlorite cake 12 to clean and disinfect toilets. A more complete description of the surfactant cake may be found in the example of a commonly owned patent application, Ser. No. 972,318, filed by Kitko, on Dec. 22, 1978. The operation of the portion of integrated dispenser 10 which is outside of dotted line 16 is described in great detail in a second commonly owned patent application, U.S. Ser. No. 002,524, filed by Dirksing, on Jan. 11, 1979, especially in FIGS. 1-8 and the accompanying text. The preceding two patent applications are incorporated herein by reference.

The portion of integrated dispenser 10 enclosed by dotted line 16, hereinafter known simply as hypochlorite dispenser 16, comprises a measuring cavity 18, an inlet conduit 20, a reservoir 22 which contains hypochlorite cake 12, a discharge standpipe 24, inlet ports 26 and 28, and outlet port 30. The dispenser may conveniently be formed from two sheets of plastic: a first sheet of plastic debossed to form channels which correspond to the pattern of the unshaded areas and lightly shaded hypochlorite and surfactant cakes of FIG. 1 and perforated to form inlet ports 26 and 28 and outlet port 30; laminated to a second, flat sheet of plastic and bonded thereto in the areas corresponding to the more heavily shaded portions of FIG. 1.

The parts of hypochlorite dispenser 16 will now be described in greater detail. Measuring cavity 18 is defined by cavity lower partition 32, cavity upper partition 34, cavity side partition 36 and cavity partition 38. Inlet ports 26 and 28, which have respective topmost points 40 and 42 and respective lowest points 44 and 46 communicate between measuring cavity 18 and a portion of the toilet tank interior which is below the highest water level of the toilet tank. Measuring cavity 18 communicates with inlet conduit 20 in the region of point 48.

Inlet conduit 20 is defined by the space between cavity partition 38 and vertical partition 50. The cavity partition 38 which separates measuring cavity 18 and inlet conduit 20 has a lower point 52 adjacent point 48. Inlet conduit 20 is separated from the uppermost region 54 of reservoir 22 by vertical partition 50 which has an uppermost point 56 which is immediately adjacent point 58 defining the region wherein inlet conduit 20 communicates with uppermost region 54 of reservoir 22.

The free air space above measuring cavity 18, as well as all other communicating air spaces above uppermost point 56 of vertical partition 50, is designated herein as head space 60. The upper portion of head space 60 is defined by upper wall 62.

Reservoir 22 is defined by lower partition 64, side partition 66, measuring cavity lower partition 32 and side partition 68. Hypochlorite cake 12 fills most of the lower portion of reservoir 22, so that at least its upper face 70 is exposed to the water in reservoir 22. As noted above, the uppermost region 54 of reservoir 22 communicates with inlet conduit 20 at point 58. Reservoir 22 has an outlet conduit 72 which communicates between reservoir 22 and discharge standpipe 24. Outlet conduit 72 is defined by cavity side partition 36 and the upper portion of side partition 68. Outlet conduit 72 is further defined by deflecting partition 74.

Discharge standpipe 24 is defined by side partition 68, dispenser side partition 76, the left-hand extremity of lower partition 64, and mouth 78 of outlet conduit 72. Discharge standpipe 24 communicates with a portion of the toilet tank below its high water level and above its low water level via outlet port 30; with head space 60 at point 80; and with outlet conduit 72 of reservoir 22 at mouth 78.

It is important to the operation of hypochlorite dispenser 16 that the following points of the dispenser should respectively be arranged from highest to lowest, in order: head space 60, uppermost point 56 of vertical partition 50; topmost points 40 and 42 of inlet ports 26 and 28; topmost point 82 of side partition 68; lowest points 44 and 46 of inlet ports 26 and 28; lowest point 52 of cavity partition 38; cavity lower partition 32; upper face 70 of hypochlorite cake 12; and outlet port 30 of discharge standpipe 24. When the dispenser is in use in a toilet tank, the dispenser is oriented as in FIG. 1 at a depth sufficient that the high water level in the toilet tank is above topmost points 40 and 42 of inlet ports 26 and 28, and so that the low water level in the toilet tank is below outlet port 30.

It will be noted from inspection of FIG. 1 that inlet ports 26 and 28 are covered by temporary partition 84, a segment of water-soluble material which covers inlet ports 26 and 28 when the dispenser is new, but which dissolves to open up inlet ports 26 and 28 shortly after the dispenser is placed within a toilet tank. It will also be noted that a small priming port 85 is provided in hypochlorite dispenser 16. Temporary partition 84, in conjunction with priming port 84 allows dispenser 16 to be self-priming, as is explained in detail at the conclusion of this description of the operation of the dispenser. (As will be explained later, temporary seal 84 and priming port 85 do not affect the operation of the dispenser after the priming operation is complete, so they are not included in FIGS. 2-8.)

Figure 2:
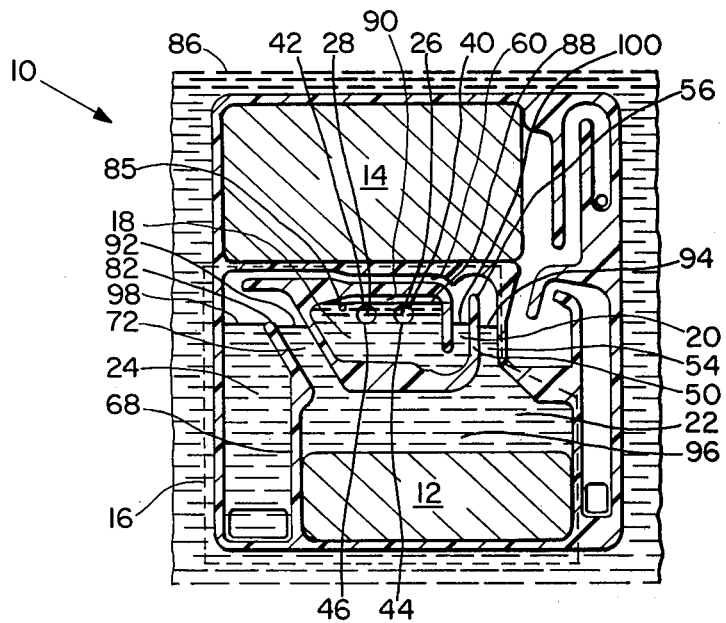
FIGS. 2 through 7 are a sequence of plan views which show the operation of the dispenser of FIG. 1 responsive to the flushing of a toilet tank in which it is immersed.
Figure 5:
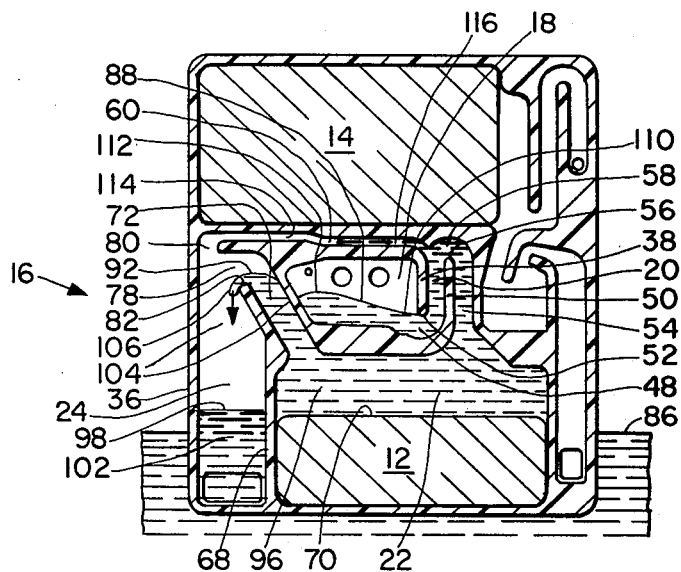
Figure 6:
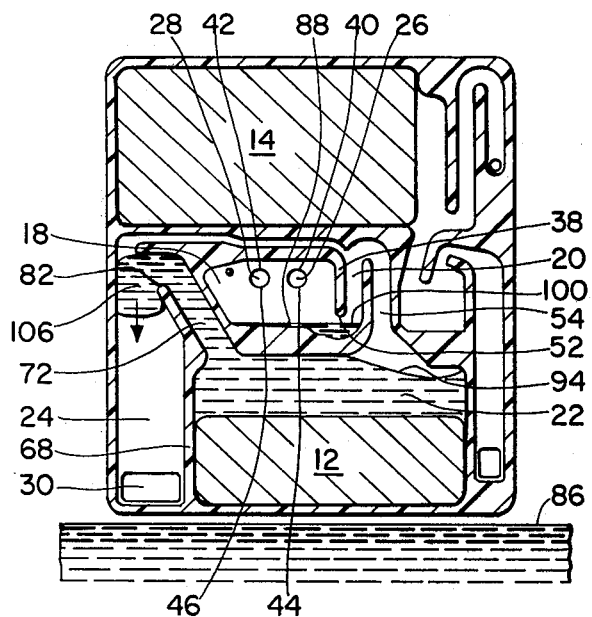
Figure 7:
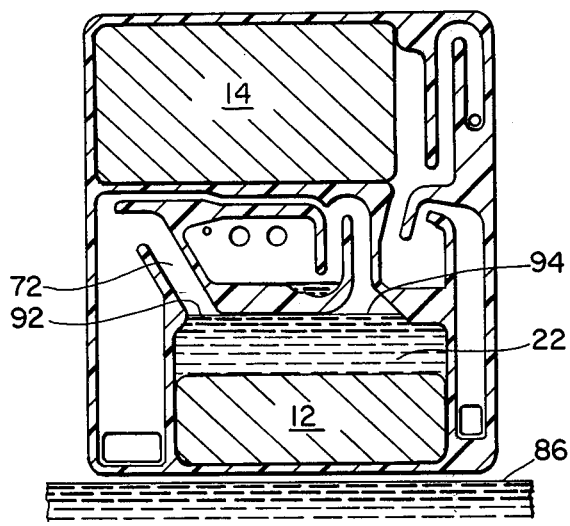

FIGS. 2-7 illustrate the operation of dispenser 16 in sequence, starting with FIG. 2 in which the dispenser is in place in a toilet which is ready to be flushed and finishing with FIG. 7 in which the toilet tank is completely flushed and ready to refill. It should be noted that in FIGS. 2 through 7 inlet ports 26 and 28 are uncovered, as is typical shortly after the dispenser is installed.

Referring first to FIG. 2, the dispenser shown in fully operational in a toilet tank which is ready to be flushed. Although in this figure the water surface 86 in the toilet tank is shown to be above the entire dispenser, it is sufficient that the high water level of water surface 86 be above topmost points 40 and 42 of inlet ports 26 and 28 in order to allow dispenser 16 to function. As shown in FIG. 2, the water surface 88 within measuring cavity 18 is approximately at the level of topmost points 40 and 42 of inlet ports 26 and 28, because water from the toilet tank can enter measuring cavity 18 via inlet ports 26 and 28 until the level of surface 88 is attained. After water surface 88 reaches topmost points 40 and 42 of inlet ports 26 and 28, the water can rise no further because to the extent that there is any head space 90 in measuring cavity 18 at this point, the air trapped in head space 90 will prevent water from entering to raise water surface 88 any further. The water surfaces 92 and 94, respectively in outlet conduit 72 and within uppermost region 54 of reservoir 22 are at the same level, since water surfaces 92 and 94 are surfaces of the same body 96 of water, and since the air space above water surface 92 and the air space above water surface 94 are in communication via head space 60. Water surface 92 is below topmost point 82 of the side partition 68, and as a result of the relation between topmost point 82 and uppermost point 56 (the latter of vertical partition 50), water surface 94 is some distance below uppermost point 56 of vertical partition 50. The surface 98 of the water within discharge standpipe 24 is at approximately the same level as lowest points 44 and 46 of inlet ports 26 and 28, and thus is below topmost point 82 of side partition 68. The water surface 100 of inlet conduit 20 is below uppermost point 56 of vertical partition 50 is approximately at the same level as water surface 88 within measuring cavity 18, although it will be understood that if there is a pressure differential between head space 90 of measuring cavity 18 and head space 60, water surfaces 88 and 100 will differ in level. As will become apparent, the water levels shown in FIG. 2 are typical of the dispenser when it is in use at the point in time when the toilet tank is completely full; the dispenser will return to this state of its own accord at the end of a flushing cycle.

Figure 3:
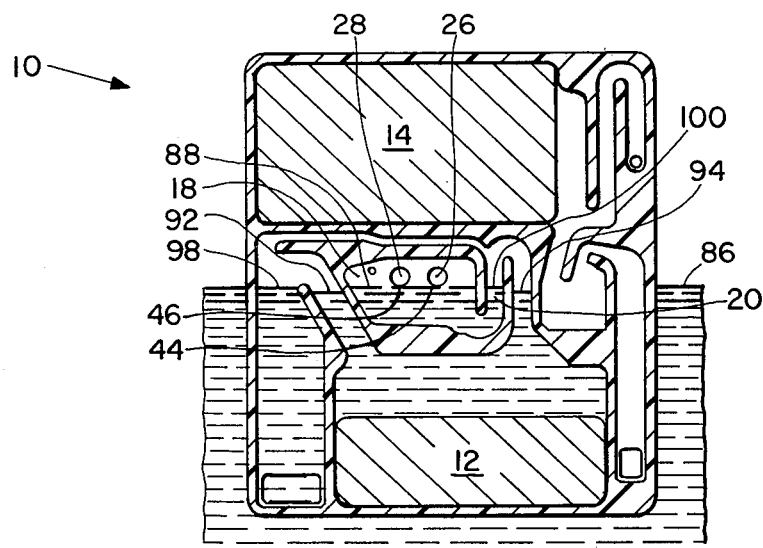

FIG. 3 shows the status of the toilet tank dispenser of FIG. 2 when the toilet has just been flushed and the water surface 86 within the tank has dropped to the level shown. At this point the water surface 86 has dropped to the level of lowest points 44 and 46 of inlet ports 26 and 28. Water surface 88 in measuring cavity 18 thus at is the same level as the water surface 86 of the tank because water will simply fall out of inlet ports 26 and 28 or inward from the toilet tank until water surfaces 86 and 88 are at the same level. The water surface 88 in measuring cavity 18 and water surface 100 of inlet conduit 20 are again at approximately equal levels, and in any event the difference in levels between water surface 88 and water surface 100 in FIG. 3 is the same as the respective difference in these water surfaces in FIG. 2. There is substantially no change in the levels of water surfaces 98, 92, and 94 responsive to the lowering of water level 86 to the extent shown in FIG. 3.

Figure 4:
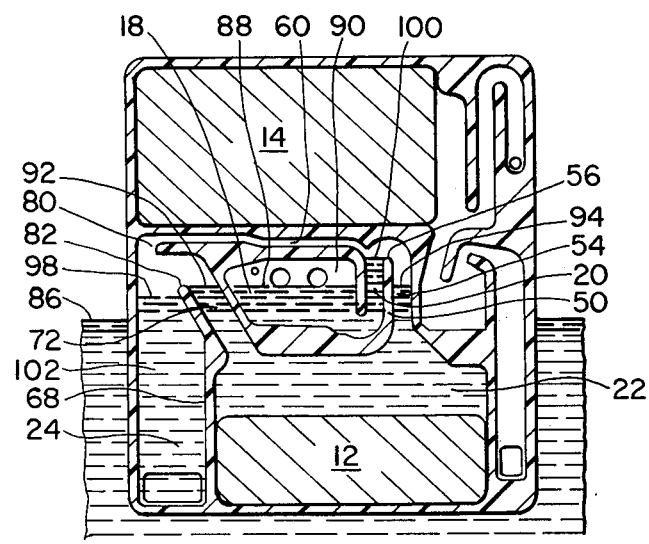

FIG. 4 shows what happens to the dispenser 16 when the water surface 86 within the toilet tank has dropped to a point slightly below the water surface 98 within discharge standpipe 24. As the water surface 86 within the toilet tank drops to somewhat below the water surface 98 within discharge standpipe 24, the pressure within head space 60 drops because communication between head space 60 and discharge standpipe 24 at point 80 allows evacuation of water 102 within discharge standpipe 24 to affect the pressure within head space 60. The pressure in head space 90 of measuring cavity 18 remains constant at this point, since head space 90 communicates with the ambient atmospheric pressure via outlet ports 26 and 28, so a decrease in the pressure in head space 60 is effective to lower the water surface 88 within measuring cavity 18 and to raise the water surface 100 within inlet conduit 20, analogous to the working of a manometer. Again, water surface 92 of outlet conduit 72 and water surface 94 of the uppermost region 54 of reservoir 22 do not move appreciably, for head space 60 communicates with both of these water surfaces. In FIG. 4, water surface 100 within inlet conduit 20 is shown to be at the same level as uppermost point 56 of vertical partition 50. As was noted above, water surface 92 is approximately at the same level as topmost point 82 of side partition 68.

FIGS. 5 shows the state of the dispenser after the water surface 86 within the toilet tank has dropped just below the level of upper face 70 of hypochlorite cake 12. As in FIG. 4, the water surface 98 within discharge standpipe 24 is just slightly above the water surface 86 in the toilet tank. Responsive to this drop of the water surface 98 within discharge standpipe 24, a substantial head space 104 is formed in discharge standpipe 24. At this point there is still no direct source of air to fill head space 104, so as a result of creation of head space 104, a considerable pressure drop is generated in discharge standpipe 24, and as a result of communication at point 80 between head space 60 and head space 104, the pressure within head space 60 also drops considerably. This pressure drop is sufficient that in response to it the water surface 100 (not shown in FIG. 5) within inlet conduit 20 exceeds the level of uppermost point 56 of vertical partition 50, so the water within inlet conduit 20 rushes over uppermost point 56 of vertical partition 50 at point 58. As a result, the water rushing from inlet conduit 20 merges with the water in uppermost region 54 of reservoir 22 and forces it downward within uppermost region 54 of reservoir 22. Responsive to this, the body of water 96 within reservoir 22 flows toward outlet conduit 72; the displaced water in outlet conduit 72 then rushes toward mouth 78 of outlet conduit 72, so that the water surface 92 in outlet conduit 72 exceeds the height of topmost point 82 of side partition 68. This creates a head of water 106 which rushes through mouth 78 of outlet conduit 72 and into discharge standpipe 24, merging with the water 102 within discharge standpipe 24. Responsive to the movement of water vertically through inlet conduit 20, the water surface 88 within measuring cavity 18 is drawn under lowest point 52 of cavity partition 38, past the point 48 of communication between measuring cavity 18 and inlet conduit 20. (The movement of water within hypochlorite dispenser 16 is shown in FIG. 5 by a series of arrows.) Responsive to this flow of water, the body of water 96 which originally resided within reservoir 22 is partially transferred out of the dispenser via outlet conduit 72 and discharge standpipe 24, so at this point hypochlorite-charged water is transferred over topmost point 82 of side partition 68, which normally blocks its egress when the dispenser is in a quiescent state. The water surface 88 within measuring cavity 18 is disrupted by the rapid egress of solution into inlet conduit 20, so that for a short time the head of water 110 adjacent cavity partition 38 is somewhat lower that the head of water 112 by cavity side partition 36.

Another design feature which is preferred in dispenser 16 is the provision of a portion of head space 60 adjacent point 80, known hereinafter as conduit portion 114, which is higher in elevation than the portion 116 of head space 60 which communicates with the region adjacent inlet conduit 20 near point 58. This prevents any substantial portion of the water from inlet conduit 20 from escaping via conduit portions 116 and 114 past point 80 and into discharge standpipe 24. A substantial flow in the latter direction is unacceptable because water taking this route will not displace any of the hypochlorite solution 96 within reservoir 22 into discharge standpipe 24.

FIG. 6 shows the hypochlorite dispenser 16 when the water surface 86 of the toilet tank is at or below the level of outlet port 30 and the flow of water within the dispenser is nearly complete. At this point, the head of water 106 within discharge standpipe 24 is free to fall through discharge standpipe 24 and to leave the dispenser via outlet port 30 to merge with the water in the toilet tank. The rush of water out of measuring cavity 18 through inlet conduit 20 has substantially ceased and the water surfaces 88 and 100 within the respective measuring cavity 18 and inlet conduit 20 are approximately equal, and are slightly below the level of lower point 52 of cavity partition 38. The flow rate of water within outlet conduit 72 has substantially stopped at this point, so that the water in head of water 106 to the left of topmost point 82 of side partition 68 will fall out of the dispenser through outlet port 30, while the water in inlet conduit 72 to the right of topmost point 82 of side partition 68 will drop back into reservoir 22 and merge with the rest of body of water 96. The water surface 94 in uppermost region 54 of reservoir 22 is shown in FIG. 6 at its lowest point.

FIG. 7 shows the dispenser after the discharge of hypochlorite solution is complete. At this point the heel of water within outlet conduit 72 has become an indistinguishable part of body of water 96 within reservoir 22, and flow has ceased within the dispenser so that water surfaces 92 and 94 are substantially equal.

Finally, when water surface 86 returns to the level of FIG. 2, discharge standpipe 24 will fill until the water surface 86 reaches lowest points 44 and 46 of inlet ports 26 and 28. At this point measuring cavity 18 will immediately fill to the level of the toilet tank water surface 86, raising the level of water surface 88 within measuring cavity 18 above lower point 52 of cavity partition 38 so that inlet ports 26 and 28 are isolated from head space 60 by a water trap. At this point water can only enter dispenser 16 through inlet ports 26 and 28, and this flow of water ceases when water surface 86 reaches topmost points 40 and 42 of inlet ports 26 and 28. The dispenser is now in the state shown in FIG. 2. As shown in FIG. 2, the body of water 96 within reservoir 22 is entirely isolated from the tank water found in measuring cavity 18 and discharge standpipe 24, so no hypochlorite ions can escape between flushes.

A comparison of FIGS. 2 and 7 in light of the preceding description will reveal that the change in water levels 92 and 94 in the respective figures is not accounted for by a flow of water into the dispenser when the toilet tank refills. This level change occurs because the walls of the dispenser, and particularly the major faces of the plastic surrounding reservoir 22 (not shown) are flexed inward in FIG. 2 but not in FIG. 7 by the water pressure of the water in the toilet tank.

In a dispenser of the type shown as hypochlorite dispenser 16, it is highly desirable to provide temporary means which allow dispenser 16 to initially fill with water to a level exceeding the height of topmost portion 82 of side partition 68 when the dispenser 16 is first inserted into a toilet tank. This self-priming function allows reservoir 22 to fill with water as soon as hypochlorite dispenser 16 is deployed, so that a hypochlorite solution can immediately begin to form in reservoir 22. If a self-priming feature is not provided, the reservoir 22, which is several times as large as the volume of water supplied by measuring cavity 18 as a result of each flush of the toilet, will not contain a full charge of hypochlorite solution until the toilet has flushed several times. As a result, delivery of the desired dose of available chlorine to the toilet tank is delayed if no provision is made to prime the dispenser initially.

FIG. 1 shows the features of a highly desirable hypochlorite dispenser 16 which is provided with self-priming means consisting of temporary partition 84 and priming port 85. When hypochlorite dispenser 16 is first placed in a toilet tank by the consumer, the dispenser contains no water, as shown in FIG. 1. At this point, temporary partition 84, which may be a portion of water-soluble tape, initially blocks inlet ports 26 and 28 to prevent the passage of air or water. At the same time a priming port 85 is provided in the dispenser. Priming port 85 is made sufficiently small that air can pass through it slowly but water cannot easily pass through it. Priming port 85 is positioned so that it is higher than topmost point 82 of side partition 68. When the hypochlorite dispenser 16 is first inserted into the water of a toilet tank, water enters the dispenser via outlet port 30. The air which is displaced by this water is vented via priming port 85. The water pressure exerted by the water entering the dispenser exceeds the water pressure tending to stop the venting of air through priming port 85 so long as the level of water entering the dispenser is below priming port 85. Since priming port 85 is somewhat higher than topmost point 82 of side partition 68, water will continue to enter the dispenser until the water level in the dispenser exceeds the level of topmost point 82, thus flooding reservoir 22 with water. Shortly after this flooding takes place, temporary partition 84 is adapted to dissolve so that water may fill measuring cavity 18 via inlet ports 26 and 28 in the manner described previously. Once inlet ports 26 and 28 are unsealed, they remain that way for the life of the dispenser, so water entering the dispenser via outlet port 30 is prevented from again exceeding the level of topmost point 82 of side partition 68 by the water trap created by water entering inlet ports 26 and 28 when the water level in the tank reaches lowest points 44 and 46 of inlet ports 26 and 28. Thus, priming port 85, which is too small to allow a substantial rate of water flow, becomes superfluous for the remainder of the life of the hypochlorite dispenser 16.

What follows is a description of the composition and manufacture of hypochlorite cakes for use in practicing the present invention.

Hypochlorite cakes useful in the present invention may most broadly be described as compositions containing a source of hypochlorite anions and a water-soluble salt which provides a second anion selected from metasilicate, carbonate, orthosilicate, or mixtures of any of the above. It is also essential that each cation which is present in the composition in a substantial amount must form a water-soluble hypochlorite, and that at least one cation which is present in a substantial amount must form an insoluble salt of the second anion which is selected. When the hypochlorite cake is put into operation in a water-containing toilet tank, most or all of the hypochlorite in the above composition will be available for dissolution in the water of the dispenser reservoir, for only cations which form water-soluble hypochlorites are present in substantial amounts in the composition. At the same time, the second anion and at least one of the cations form a substantial quantity of a water-insoluble substance which takes the form of a porous matrix. The inventors have found that when the present invention is practiced as taught herein, the presence of insoluble components in the hypochlorite cake does not prevent the hypochlorite from escaping altogether. In fact, the hypochlorite ions are found to migrate from the hypochlorite cake more slowly and much more evenly than is true for prior cake-form hypochlorite compositions. The insoluble components also displace and entrain water in the dispenser so that its pourable fluid capacity is maintained or slightly reduced as hypochlorite is depleted from the cake. Thus, the essential components of the hypochlorite cake are hypochlorite anions, the salt of a second anion selected from the group described above and cations which form water-soluble hypochlorites, wherein at least one cation forms a water-insoluble porous matrix when combining with said second anion as the hypochlorite cake is exposed to water.

While the essential features of the hypochlorite cake composition are the abilities to provide water-soluble hypochlorite and to form an insoluble porous matrix, the preferred hypochlorite cake compositions have one or more of several additional properties. For example, it is highly preferable to provide a porous insoluble matrix which swells somewhat while the hypochlorite cake is in use. This reduces the pourable fluid capacity of the reservoir in a toilet tank dispenser. A moderate decrease in the pourable fluid capacity of the reservoir is highly desirable in order to limit the amount of hypochlorite solution which is formed in the dispenser during the latter stage of the life of the hypochlorite cake.

Figure 8:
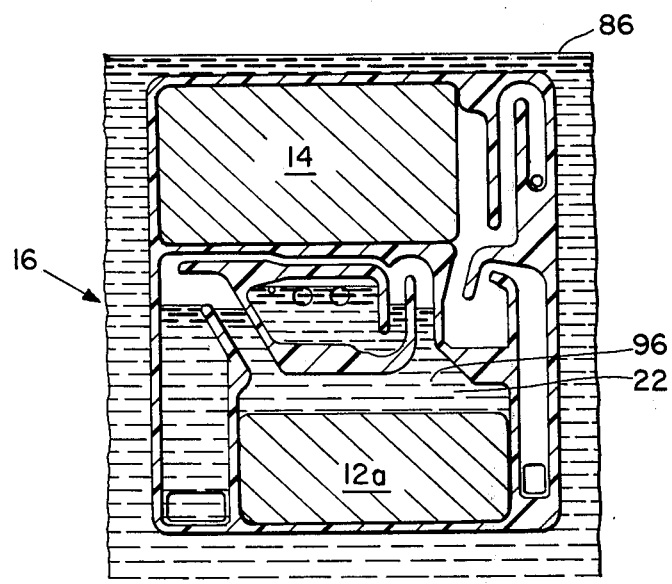
FIG. 8 is another plan view of the dispenser of FIG. 1 which shows the expansion of the hypochlorite cake in a preferred mode of the invention after the dispenser has been in use for a period of time.

FIG. 8 illustrates a preferred embodiment of the present invention in which used hypochlorite cake 12a has expanded somewhat, thus decreasing the pourable fluid capacity of the dispenser. This expansion of used hypochlorite cake 12a is the result of the contact of the hypochlorite cake with body of the water 96 in reservoir 22, and the consequent formation of the insoluble matrix as described above.

Another highly desirable feature of a hypochlorite cake composition is that it should contain a very stable hypochlorite salt, but one that is highly mobile and thus readily available to form hypochlorite solutions. Calcium hypochlorite and lithium hypochlorite are among the most stable hypochlorites, but sodium hypochlorite is much more easily dispersed into the reservoir to form hypochlorite solutions. The problem of achieving the mobility of sodium hypochlorite while retaining the stability of calcium and lithium hypochlorites may be solved by providing a salt system containing calcium or lithium hypochlorite and the sodium salt of a second anion which forms highly insoluble calcium or lithium salts. When water impinges on the hypochlorite cake, the calcium or lithium ions which are to form the highly insoluble salt will do so, thus freeing the sodium cations originally associated with the second anion to form highly mobile sodium hypochlorite in solution. This ion exchange mechanism is discussed in U.S. Pat. No. 3,234,141, issued to Robson on Feb. 8, 1966, although the use therein is in a much different context.

A third highly desirable property of a hypochlorite cake according to the present invention is that it should provide a relatively high pH to the hypochlorite solution. Representative of prior art relating to this advantage is U.S. Pat. No. 3,843,548, issued to James on Oct. 22, 1974.

Finally, it will frequently be highly desirable that any of a wide variety of diluent materials be incorporated into the hypochlorite cakes of the present invention. Since toilet tank dispensers of the present invention are intended to be used for a relatively extended period of time in a home toilet tank without any maintenance by the consumer, it will be apparent that the compositions must deliver a relatively low, yet effective, concentration of hypochlorite to the toilet tank. Diluent materials satisfy this need by slowing the dissolution of the hypochlorite components of the hypochlorite cake, as well as by preventing large quantities of hypochlorite from dissolving when the hypochlorite solution is maintained in the reservoir for a long period, for example, when the toilet is flushed infrequently.

The components of a hypochlorite cake according to the present invention will now be described in terms of the concentration ranges and preferred concentrations of particular species, expressed in terms of percent of hypochlorite cake weight.

As already noted above, the composition will contain a source of hypochlorite ion. The hypochlorite ion may be present in the composition at a level of 5% to 84% by weight (hereinafter all percentages are by weight unless otherwise specified), preferably 14% to 33%, most preferably 22.5%.

The water-soluble salt of the second anion noted above, which is to form an insoluble porous matrix in combination with one of the cations present, is the compound of an anion selected from the group consisting of metasilicate, carbonate, orthosilicate, and mixtures of any of the above, and of any suitable cation which produces a water-soluble salt (with the limitation that it must form a water-soluble hypochlorite). The water-soluble salt of the second anion should be present in an amount of from about 4% to 30%, preferably 8% to 20% of the composition.

Another species which should be present in the hypochlorite cake is the cation which is to form the insoluble porous matrix with the second anion noted above. In its broadest aspect, this cation may be any cation which forms an insoluble compound with the chosen second anion, so long as the cation does not form an insoluble hypochlorite or cause the decomposition of hypochlorite. Illustrative of the cations which form insoluble salts of various species of the second anion are as follows: For metasilicate, the lithium, magnesium, calcium, strontium, and barium salts are insoluble, but the sodium and potassium salts are soluble; for carbonate, the beryllium, magnesium, calcium, strontium, and barium salts are insoluble, the potassium salts are very soluble, the sodium salt is somewhat soluble and the lithium salt is slightly soluble (the solubility of lithium and sodium carbonates is sufficiently high to render them soluble in preferred embodiments of the present invention); the orthophosphates of lithium and magnesium are insoluble, while the sodium and potassium salts are soluble; the orthosilicates of lithium and magnesium are insoluble, while those of sodium are soluble. Thus, depending on the choice of a matrix-forming anion, the cation which is to participate in the creation of an insoluble matrix may initially be selected from lithium, magnesium, calcium, strontium, barium, and beryllium. Of these, only lithium, magnesium, and calcium are known to form soluble hypochlorites, so these three cations are highly preferred as species which may be used herein to form insoluble matrices. However, the inventors do not limit themselves to these particular cations, because any other cations which form water-soluble hypochlorites and which form insoluble metasilicates, carbonates, phosphates, or orthosilicates may easily be incorporated into the present compositions to produce the same result. This cation will typically be provided as the cation of a hypochlorite salt, but may also be provided by a diluent material as described below. It is preferred that this cation should be present in a stoichiometric excess with respect to the available quantity of the second anion which is selected.

The hypochlorite cake will now be defined in terms of salts from which it may be compounded.

First, as noted above, the hypochlorite salts known to the inventors are lithium, sodium, potassium, magnesium, and calcium hypochlorites. Of these, the sodium salt is less preferred because it is not stable as a highly concentrated or pure substance. As a result, sodium hypochlorite cannot easily be added to the tablet directly as a dry salt. Preferred hypochlorite salts are the lithium and calcium hypochlorites or their mixtures. These salts are available commercially in more concentrated form than is sodium hypochlorite, so that they may be used in the formulation of hypochlorite cake compositions which are stable and have a long shelf life. The lithium and calcium hypochlorites are also preferred over sodium hypochlorite because lithium and calcium cations formed insoluble metasilicates and orthosilicates, and calcium in particular forms insoluble carbonates as well, so by incorporating lithium or calcium hypochlorites in the composition, two ions essential to the composition may be provided by a single chemical compound. An especially preferred hypochlorite salt for use herein is a mixture of lithium and calcium hypoclorites. In a copending application filed by one of the present inventors (U.S. Ser. No. 897,478, filed by Nyquist on April 18, 1978) certain mixtures of lithium and calcium hypochlorites are described which have been found to provide a relatively constant level of available chlorine in toilet tank dispensers despite the variation in toilet tank water temperatures in typical toilets. Particular weight ratios of lithium to calcium hypochlorite which may be used are from 0.17:1 to 0.47:1.

The level of hypochlorite ions in the compositions herein is 5% to 84%, preferably 14% to 33%, and most preferably 22.5% by weight. If the hypochlorite is to be supplied by the mixtures of lithium and calcium hypochlorite described above, the broadest range of lithium hypochlorite is about 1% to about 31% by weight, and the broadest range of calcium hypochlorite is about 4% to 82% by weight. An appropriate source of calcium hypochlorite for use herein is a product known as High Test Hypochlorite or "HTH", a hypochlorite source typically containing a maximum of 71% calcium hypochlorite by weight which is available from Olin Corporation, 120 Long Ridge Rd., Stamford, Connecticut 06904. A commercial source of lithium hypochlorite is a composition known as "Form 2," containing about 30% pure lithium hypochlorite, available from Lithium Corporation of America, Bessemer City, North Carolina 28016, a subsidiary of Gulf Resources and Chemicals Corporation. Since the percentages by weight of calcium hypochlorite and lithium hypochlorite refer to the pure compounds, it should be noted that the impurities in these compositions are considered to be diluent salts in this specification. A further description of the HTH and Form 2 hypochlorites is contained in the application of Nyquist cited above.

The second salt which is required in formulations of the present composition is a water-soluble source of the anionic species known herein as the second anion, which is to participate in the formation of an insoluble porous matrix when the composition is exposed to the water of the reservoir of the dispenser. Most broadly, this salt may be any salt of a group of anions selected from metasilicate, carbonate, orthosilicate, and mixtures thereof. Preferred salts for use as a water-soluble salt of the second anion in the composition are water-soluble salts of metasilicate, carbonate, orthosilicate, or mixtures thereof. Specific examples of such salts are as follows: sodium metasilicate, potassium metasilicate, sodium carbonate, potassium carbonate, and sodium orthosilicate. These water-soluble salts react with the preferred mixtures of calcium and lithium hypochlorites to form insoluble calcium or lithium salts. Such species of the water-soluble salt of the second anion, in particular the sodium salts, provide a highly soluble hypochlorite upon ion exchange between the hypochlorite salt originally in the composition and the second salt. Preferred soluble salts of the second anion for use herein are sodium metasilicate and sodium carbonate. Of these, sodium metasilicate is most preferred. Sodium metasilicate, when used in the proportions noted in the examples, provides an insoluble matrix which expands somewhat in order to actually reduce the pourable fluid capacity of the dispenser as the hypochlorite ion is exhausted. Sodium carbonate also forms an expanding matrix. The soluble salt of the second anion may be present in the composition in a range of from 4% to 30% by weight, preferably 8% to 20% by weight.

Diluent materials for incorporation herein may be selected from any of a wide variety of salts of cations which form water-soluble hypochlorites. Diluent materials for use in the present invention may be selected, for example, from a wide variety of materials, provided that the diluent materials do not supply a substantial proportion of cations which form water-insoluble or unstable hypochlorites or facilitate the decomposition of hypochlorite ion. These diluent materials are desirably water-soluble, although they may supply cations which form insoluble salts with the second anion. It will be noted that the diluent material might not be a salt without departing from the scope of the present invention, provided that it does not react with hypochlorite or otherwise interfere with the operation of the present invention. A general category of materials which may be used as diluent materials are the alkali metal or alkaline earth metal chlorides, fluorides, chlorates, hydroxides, sulfates, nitrates, and so forth. Specific examples of such diluent salts which are soluble in water are: lithium fluoride, chloride, chlorate, sulfate, hydroxide, and nitrate; potassium fluoride, sulfate, chloride, chlorate, hydroxide, and nitrate; magnesium chloride, sulfate, chlorate, and nitrate; and calcium chloride, chlorate, and nitrate. A preferred material is sodium chloride, primarily because of its high solubility, low cost, and ability to provide sodium ions to the composition. The level of addition of the diluent material will vary somewhat depending on the solubility of the particular species, but the diluent materials will be present at a level between about 0% and 90%, preferably 34% to 76% by weight of the composition.

What follows is a description of the manufacture of hypochlorite cakes according to the present invention, and their incorporation in passive dosing toilet tank dispensers in order to complete the invention.

If, for example, an 85 gram hypochlorite cake is to be produced, the dry ingredients are mixed in the desired proportions to form a substantially uniform mixture of the components of the cake. The mixture is then compressed in a tablet press, for example, a Stokes Model R Tablet Press, at a compaction which may be about 2.5 to 3.5 tons per square inch (352 to 492 kilograms per square centimeter). The resulting cake may desirably have a density of about 1.7 grams per cubic centimeter and a volume of about 50.7 cubic centimeters. The exact dimensions of the cake will depend on the dimensions of the bottom portion of the reservoir of the toilet tank dispenser, and on the ratio of initial tablet volume to reservoir volume which is selected. If the total reservoir capacity is about 100 milliliters, and the cake is intended to fill about 50% of the reservoir, the cake should have a horizontal cross sectional area which is nearly equal to the horizontal cross sectional area of the dispenser, so as to substantially fill the entire bottom of the dispenser. In such a case the height of the cake may desirably be sufficient to provide an initial cake volume of about 50 cubic centimeters.

In order to incorporate the hypochlorite cake in the hypochlorite dispenser, the hypochlorite cake is first formed with suitable proportions, the thermoformed portion of the hypochlorite dispenser is formed separately, and the hypochlorite cake is placed within the part of the reservoir which will be on the bottom when the hypochlorite dispenser is in use. The hypochlorite dispenser is then assembled with the hypochlorite cake in placed by superimposing a flat portion of material over the thermoformed portion of the dispenser and by attaching the thermoformed and flat portions of the dispenser at the required points to form a completed hypochlorite dispenser, as by ultrasonic welding confined to the points of contact of the respective portions of the dispenser.

As previously mentioned, in a preferred mode of the present invention the hypochlorite dispenser is formed as one part of an integrated dispenser which also provides means to dispense at least one other ingredient to a toilet tank. The use of such an integrated dispenser comprising a plurality of dispensing means is particularly advantageous in the event that certain ingredients to be dispensed into the toilet tank cannot be stored with hypochlorite sources in concentrated cake form without engaging in unwanted reactions. For example, a commonly assigned patent application, U.S. Ser. No. 972,318, filed on Dec. 22, 1978, by David Kitko, describes a solid, compacted cake containing dye and other ingredients which may be inserted into the integrated dispenser 10 of FIG. 1 as surfactant cake 14 in order to provide dyes, perfumes, surfactants, and the like to a toilet tank. These ingredients may then be codispensed with hypochlorite solutions to perform their respective functions, even though many ingredients in these categories cannot be formulated in a dry cake which contains hypochlorites in concentrated form. In the event that plural cakes of ingredients are to be incorporated into a dispenser, all of the cakes are placed in the integrated dispenser before the dispenser portions are joined.

The relation of reservoir size to hypochlorite cake size in the hypochlorite dispenser is important to the operation of the present invention, since it is necessary to deliver a useful concentration of hypochlorite to the toilet tank, and it is necessary to avoid creating an unduly large pourable fluid capacity in the dispenser as the cake is used up. It is also important, in the event that a swelling hypochlorite cake is used, to produce a hypochlorite cake which is of such a size and composition that it expands no more than a known maximum extent so that the reservoir does not become of insufficient effective size to dispense the appropriate amount of hypochlorite, and additionally so that the passages communicating with the reservoir are not in danger of being obstructed by the swelling hypochlorite cake. Thus, in order to practice the present invention, it is preferred that the tablet occupy about 30% to 70% (preferably about 40% to 65%) of the reservoir volume when new, and it is important that the cake be capable of swelling while in use to no more than about 70% of the volume of the reservoir, thus precluding flow blockage and ensuring that the pourable fluid capacity of the reservoir does not fall below about 30% of the initial reservoir pourable fluid capacity. FIG. 8 shows hypochlorite cake 12a in an expanded state within reservoir 22 of hypochlorite dispenser 16. At the same time, in order to achieve the benefits of the present invention, it is necessary that the hypochlorite cake must not be reduced in size to less than about 30% of the reservoir capacity or increased in porosity to the extent that the pourable fluid capacity of the dispenser in use exceeds the initial pourable fluid capacity of the dispenser.

EXAMPLE I

In this example two hypochlorite cakes were formed, Formula A being a cake which does not embody the present invention, and Formula B being a cake which embodies the present invention. The ingredients of the respective cakes were as follows:

TABLE I

| Component | Formula A, % | Formula B, % |
|---|---|---|
| HTH: | | |
| $Ca(OCl)_2$ | 27.1 | 22.2 |
| Impurities | 11.6 | 9.6 |
| Form 2: | | |
| LiOCl | 7.7 | 8.0 |
| Impurities | 17.0 | 17.9 |
| NaCl | 27.1 | 28.2 |
| $Na_2SO_4$ | 9.4 | 0 |
| $Na_2SiO_3$ | 0 | 14.1 |
| | 100.0 | 100.0 |

85 grams of each formula were pressed into hypochlorite cakes with densities of about 1.7 grams per cubic centimeter in a Stokes Model R Tablet Press, available from the Stokes Division of Pennwalt, Inc. The hypochlorite cakes were approximately 8.9 centimeters by 3.8 centimeters by 1.5 centimeters and each had the shape of a rectangular parallelepiped. A pressure of 422 kilograms per square centimeter was used in the Stokes press. The resulting hypochlorite cake had a volume of about 50.7 cubic centimeters. When incorporated in dispensers of the type shown in FIG. 1, each hypochlorite cake filled approximately one-half of the hypochlorite dispenser reservoirs. The dispensers with their respective hypochlorite cakes were then subjected to a flushing test.

In the flushing test the dispensers were placed in the tanks of essentially ordinary toilets of the type used in households. Each toilet was flushed 4 times between 8:00 and 8:30 AM and once at each of the following times: 10:00 AM; 2:00 PM; 2:30 PM; 4:30 PM; 5:00 PM; 6:20 PM; 7:50 PM; 9:20 PM; 10:50 PM; and 12:15 AM in order to simulate the flushing times and frequency of the toilet of an ordinary consumer. The toilets were allowed to stand overnight without flushing and the flushing cycle was repeated from day to day during the course of the test. At numerous occasions during the course of the test the available chlorine delivered to the toilet bowl was measured. It was found that the Formula B cake delivered a more steady level of hypochlorite during the course of the test than did the Formula A cake, which produced a much higher hypochlorite level early in the test. This illustrates that a more even delivery of available chlorine is provided by the hypochlorite cake formulation of the present invention.

EXAMPLE II

In this example the hypochlorite cakes of the present invention are shown to reduce the adverse effects of premature disposal of toilet tank dispensers which still contain hypochlorite solutions. Hypochlorite cakes embodying formulas A and B were compounded and placed in dispensers as above. The flushing protocol described above was practiced for two days, and the dispensers were then left in the toilet tanks for another two days without flushing the toilets in order to allow the available chlorine inside the dispensers to reach a maximum. The solutions from each dispenser were poured out and weighed to determine the pourable fluid capacity of each dispenser, and the available chlorine as a percentage of solution weight was also measured. The respective solutions were then brought into intimate contact with an excess of paper towels to simulate contact between the hypochlorite and the materials to be found in an ordinary waste basket. Over a period of 30 minutes, the maximum reaction temperature and the number of millimoles of chlorine gas released were measured. The results are shown in Table 2.

TABLE 2

| Formula | PFC | AvCl$_2$ | T | mMoles Cl$_2$ |
|---|---|---|---|---|
| A | 60 gm | 11.77% | 97° C. | 4.3 |
| B | 47 gm | 9.28% | 65° C. | 1.6 |

(In Table 2, "PFC" stands for pourable fluid capacity in grams provided by the dispenser in question; "AvCl$_2$" indicates the available chlorine as a percent of solution weight provided by the solutions of the respective dispensers; "T" indicates the maximum temperature observed during the reaction of the solution with paper towels; and "mMoles Cl$_2$" indicates the number of millimoles of chlorine gas which were released during the reaction of the solution with paper towels.) It is apparent from the data in Table 2 that by practicing the present invention the magnitude of the potential hazard to consumers which could result from premature disposal of toilet tank dispensers of the type described herein is greatly reduced, for the amount of chlorine released is reduced by almost two-thirds and the reaction temperature is reduced by more than 30° C. This illustrates that the improved compositions of the present invention, when used in conjunction with a toilet tank dispenser of the type described herein, provides a much safer consumer product which is still effective to deliver hypochlorite to a toilet tank.

We claim:

1. In a dosing dispenser comprising a reservoir; a cake containing hypochlorite within said reservoir; and means to allow a volume of water to enter said reservoir contacting and immersing said cake, dissolve a portion of said hypochlorite and be contained therein for release at a later time; the improvement wherein said cake comprises an effective amount of a source of hypochlorite and at least one component which when exposed to water is capable of forming an insoluble, porous matrix which entrains and displaces a portion of said water in said reservoir while allowing said hypochlorite to gradually dissolve, whereby to prevent an increase in the pourable fluid capacity of said reservoir as the hypochlorite in said cake is exhausted.

2. The invention of claim 1, wherein said cake containing hypochlorite is further characterized as a composition comprising the following components, expressed in percentages by weight:
   a. 5% to 84% of a hypochlorite anion;
   b. 4% to 30% of a water-soluble salt of a second anion selected from metasilicate, carbonate, and orthosilicate; and
   c. 0% to 90% of a diluent material;
wherein each cation in the composition is capable of forming a water-soluble hypochlorite salt, and wherein at least one cation in the composition is capable of forming an insoluble matrix of said second anion.

3. The invention of claim 2 wherein said hypochlorite anion is supplied in the form of a water-soluble hypochlorite salt selected from the hypochlorites of calcium, lithium, magnesium, and mixtures thereof.

4. The invention of claim 3 wherein said hypochlorite salt is a mixture of lithium hypochlorite and calcium hypochlorite, present in a weight ratio of lithium hypochlorite to calcium hypochlorite between 0.17:1 and 0.47:1.

5. The invention of claim 2 wherein said hypochlorite anion comprises 14% to 33% of the composition.

6. The invention of claim 2 wherein said water-soluble salt of the second anion is selected from sodium metasilicate and sodium carbonate.

7. The invention of claim 6 wherein said water-soluble salt of the second anion comprises sodium metasilicate.

8. The invention of claim 2 wherein said water-soluble salt of the second anion comprises 8% to 20% by weight of the composition.

9. The invention of claim 2 wherein said diluent material is a water-soluble salt.

10. The invention of claims 4, 8 or 9, further characterized as comprising:
   a. about 22% calcium hypochlorite;
   b. about 8% lithium hypochlorite;

c. about 14% sodium metasilicate; and d. diluent materials.

11. In a dosing dispenser adapted to deliver a hypochlorite solution to a toilet tank, said dispenser comprising a reservoir; a cake containing hypochlorite within said reservoir; and means to allow a fixed volume of water to enter said reservoir, dissolve a portion of said hypochlorite anion to form a quantity of said hypochlorite solution, and be held within said reservoir until released to the toilet tank by means responsive to the subsequent flushing thereof, the improvement wherein said cake is a tableted mixture comprising:

a. 5% to 84% by weight of hypochlorite ion supplied by a salt selected from calcium hypochlorite, lithium hypochlorite, and mixtures thereof;

b. 4% to 30% by weight of a water-soluble metasilicate salt; and c. 0% to 90% by weight of a diluent material;

wherein substantially all the cations present in the composition are capable of forming water-soluble hypochlorite salts.

* * * * *

UNITED STATES PATENT AND TRADEMARK OFFICE
CERTIFICATE OF CORRECTION

PATENT NO. : 4,281,421
DATED : August 4, 1981
INVENTOR(S) : J.D. Nyquist; D.J. Kitko; R.F. Stradling, Jr.

It is certified that error appears in the above-identified patent and that said Letters Patent are hereby corrected as shown below:

Col. 1, lines 33 and 34, "receiver" should be -- reservoir --.
Col. 7, line 9, "in" should be -- is --.
Col. 7, line 42, after "50" and before "is", insert -- and --.
Col. 15, line 6, after "nitrate;" insert -- sodium fluoride, chloride, sulfate, chlorate, hydroxide, and nitrate;"
Col. 15, line 51, "placed" should be -- place --.

Signed and Sealed this

Twenty-ninth Day of December 1981

[SEAL]

Attest:

GERALD J. MOSSINGHOFF

Attesting Officer

Commissioner of Patents and Trademarks